(12) United States Patent
Obel

(10) Patent No.: US 7,203,542 B2
(45) Date of Patent: Apr. 10, 2007

(54) IMPLANTABLE BIVENTRICULAR CARDIAC STIMULATOR WITH CAPTURE MONITORING BY IECG ANALYSIS

(75) Inventor: Martin Obel, Danderyd (SE)

(73) Assignee: St. Jude Medical AB, Jarfalla (SE)

( * ) Notice: Subject to any disclaimer, the term of this patent is extended or adjusted under 35 U.S.C. 154(b) by 51 days.

(21) Appl. No.: 10/726,246

(22) Filed: Dec. 2, 2003

(65) Prior Publication Data

US 2004/0116974 A1  Jun. 17, 2004

(30) Foreign Application Priority Data

Dec. 16, 2002 (SE) .................................... 0203724

(51) Int. Cl.
  *A61N 1/00* (2006.01)
(52) U.S. Cl. ..................................... 607/27
(58) Field of Classification Search .................. 607/25, 607/27, 28; 600/510
  See application file for complete search history.

(56) References Cited

U.S. PATENT DOCUMENTS

| 4,387,717 | A | 6/1983 | Brownlee et al. |
| 5,497,780 | A | 3/1996 | Zehender |
| 5,740,811 | A | 4/1998 | Hedberg et al. |
| 6,108,577 | A | 8/2000 | Benser |
| 6,128,535 | A | 10/2000 | Maarse |
| 6,148,234 | A | 11/2000 | Struble |
| 6,473,647 | B1 * | 10/2002 | Bradley ........................ 607/27 |
| 6,493,586 | B1 * | 12/2002 | Stahmann et al. ............ 607/27 |
| 6,697,673 | B1 * | 2/2004 | Lu ............................... 607/28 |
| 6,751,504 | B2 * | 6/2004 | Fishler ........................ 607/25 |
| 6,810,284 | B1 * | 10/2004 | Bradley ....................... 600/510 |
| 2001/0049542 | A1 | 12/2001 | Florio et al. |
| 2001/0049543 | A1 | 12/2001 | Kroll |

FOREIGN PATENT DOCUMENTS

| WO | WO 99/29368 | 6/1999 |
| WO | WO 01/74441 | 10/2001 |
| WO | WO 02/36000 | 5/2002 |

OTHER PUBLICATIONS

"ECG Characteristic of Simultaneous Biventricular Stimulation in Canines," McVenes et al., (PACE), vol. 20, Apr. 1998, Part II (Abstract 416). p. 893.

* cited by examiner

*Primary Examiner*—George Manuel
(74) *Attorney, Agent, or Firm*—Schiff Hardin LLP

(57) ABSTRACT

In a cardiac stimulating device for biventricular stimulation, an intracorporeal ECG signal obtained from measuring electrode leads located outside of the heart is used for monitoring capture of the right and left ventricles. If loss of capture is detected in any of the ventricles then the pacing pulse energy will be adjusted to obtain complete biventricular capture.

14 Claims, 4 Drawing Sheets

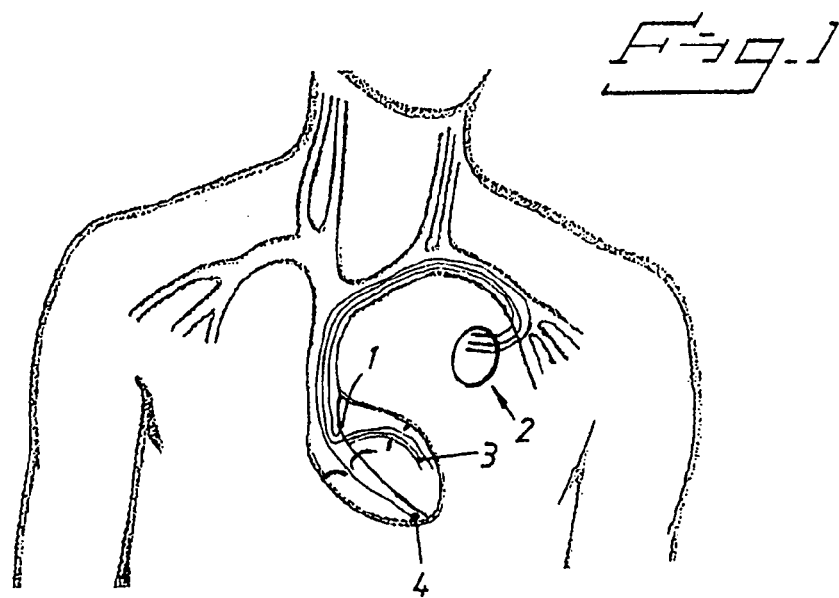
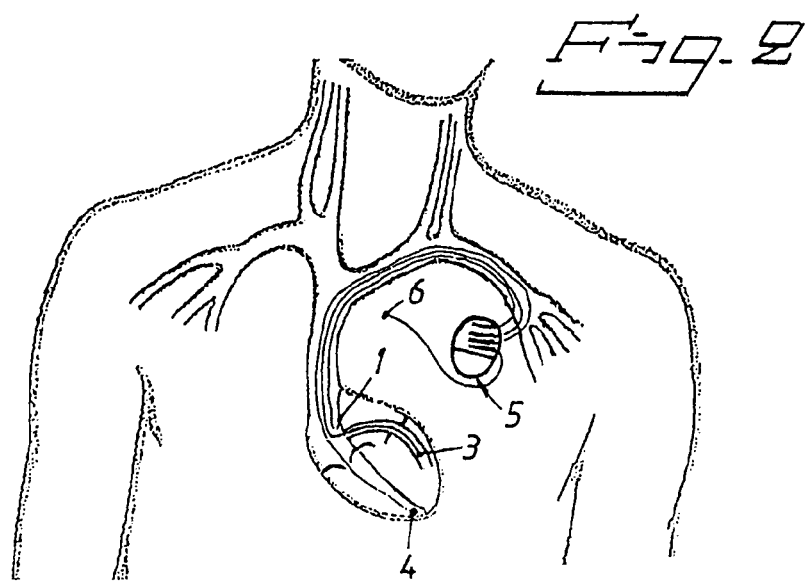

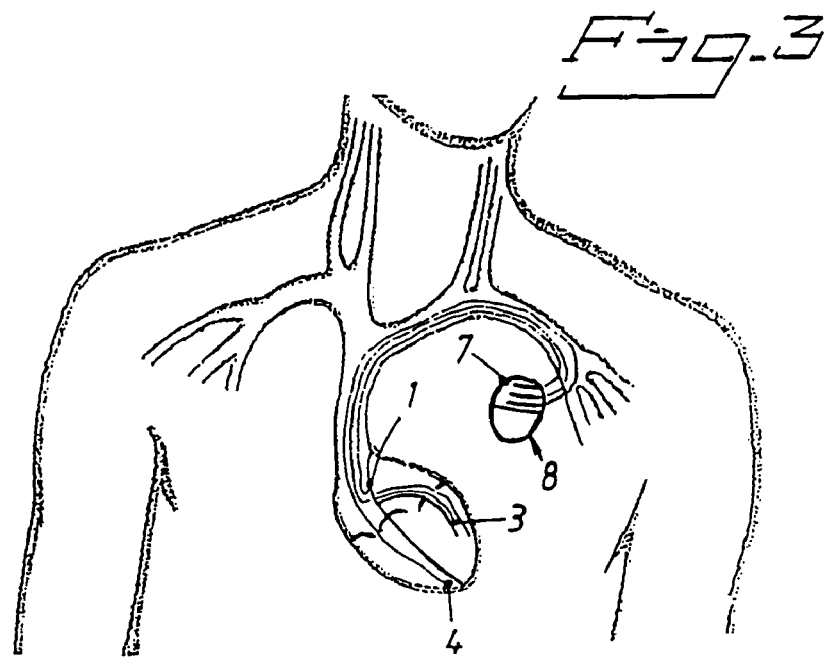
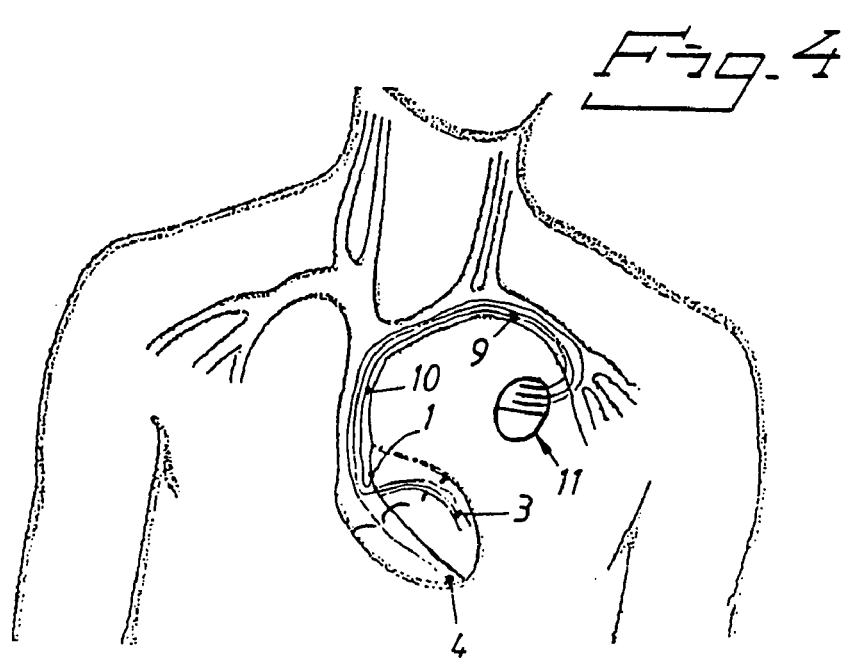

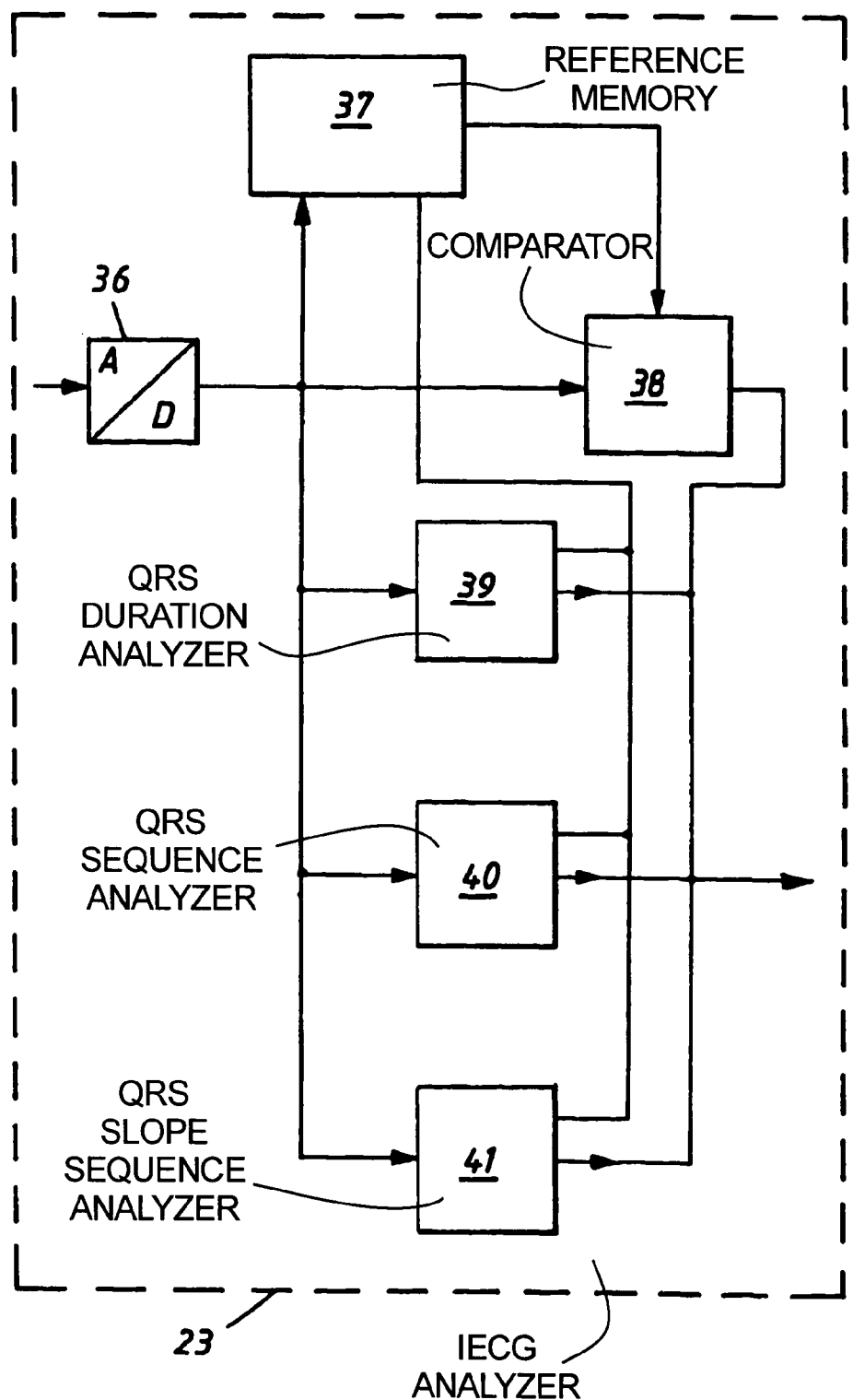

IMPLANTABLE BIVENTRICULAR CARDIAC STIMULATOR WITH CAPTURE MONITORING BY IECG ANALYSIS

BACKGROUND OF THE INVENTION

1. Field of the Invention

The present invention relates to an implantable cardiac stimulating device and specifically a biventricular pacemaker capable of monitoring capture via implanted ventricular electrodes. The invention is also applicable for an Implantable Cardioverter Defibrillator, ICD, comprising a biventricular pacemaker.

2. Description of the Prior Art

Most pacers stimulate the right ventricle of the heart but it is also known to stimulate the left ventricle. In particular, for treatment of congestive heart failure combined with ventricular dyssynchrony, it is known to stimulate both ventricles, in order to optimize the hemodynamic performance of the heart.

The improvement in hemodynamic performance that can be obtained is due to improved synchronization between the right and left ventricles. If capture is lost on any of the two ventricular stimulating electrodes the beneficial effect of the biventricular pacing therapy is lost.

U.S. Pat. No. 5,740,811 discloses a device and method to synthesize an ECG that in appearance can be substituted for a surface ECG. The synthesized ECG is based on endocardial signals obtained from pacemaker heart electrode leads.

United States Patent Application Publication 2001/0049542 discloses a biventricular pacemaker in which a bi-chamber composite cardiac signal is analyzed to determine if biventricular capture is present.

U.S. Pat. No. 6,148,234 discloses a biventricular pacing system adapted to determine capture or not in both ventricular chambers. Loss of capture in one chamber is determined if an R-wave is detected in that particular chamber during a refractory period after the stimulation pulses.

United States Patent Application 2001/0049543 discloses a biventricular pacemaker utilizing a cross-chamber stimulation method. Biventricular capture can be determined in a cross chamber sensing configuration such as with a ring-to-ring electrode configuration.

PCT Application WO 01/74441 discloses an apparatus and method for verifying capture by a selected electrode in a multi-site pacemaker. A switching circuit switches the input of an evoked response channel to an unselected electrode. The presence or absence of capture is determined from the output of the evoked response sensing channel.

PCT Application WO 99/29368 discloses an implantable device that automatically verifies capture. During predetermined periods, the device utilizes two or more pacing/sensing electrodes positioned within an electrically continuous area of the heart, with one electrode being used to provide a pacing stimulus and the other electrodes being used to determine capture.

An Abstract in Pace "ECG characteristics of simultaneous Biventricular Stimulation in Canines" by Rick McVenes and Melissa Christie discloses that biventricular capture gives shorter QRS and QT durations and that the paced QRS axis is affected depending on whether there is single site or dual site biventricular capture. The abstract was published in PACE, Vol. 21, April 1998, Part II, page 893.

A problem with known biventricular pacemakers equipped with features to assure capture after stimulation pulses is that it is difficult to verify capture on every beat particularly if the pacemaker can operate with a delay between the stimulation of the first ventricle and the second ventricle. The reason is that the stimulation pulse to the second ventricle may make it impossible to detect capture from the stimulation pulse delivered to the first ventricle. After a delivered stimulation pulse the evoked response detection window typically ends 50–100 ms after the stimulation and a second stimulation pulse delivered during this period will make it difficult to detect the evoked response from the first stimulation pulse.

SUMMARY OF THE INVENTION

An object of the present invention is to provide an implantable biventricular cardiac stimulating device wherein capture is monitored via the implanted ventricular electrodes in a manner that avoids the aforementioned problems associated with known devices.

The inventive device utilizes the fact that, as indicated above, loss on the right or on the left ventricle can be easily determined by a relatively uncomplicated analysis of the surface ECG. If there is a loss on one of the two stimulating electrodes there will be a significant change in the surface ECG morphology.

In the inventive device an intracorporeal ECG signal obtained from a location inside the body but outside of the heart is used instead of a regular surface ECG. A normal ECG signal represents the electrical activity of the heart observed at a location on the body surface. The most significant factor that controls the morphology of an ECG is the direction and distance to the heart. An intracorporeal ECG signal may be relatively similar to a surface ECG signal if the direction and distance to the heart are similar.

According to a first embodiment of the invention the intracorporeal ECG is sensed at measuring points outside of the heart but inside the body after delivery of a biventricular stimulation. At least one characteristic of the evoked intracorporeal QRS is analyzed to determine if biventricular capture is present. Possible characteristics for the analysis are e.g. QRS duration or QRS morphology.

According to a further embodiment the intracorporeal ECG is sensed between a measuring point located on the connector top and the pulse generator encapsulation.

According to a further embodiment the intracorporeal ECG is sensed between a short non-endocardial electrode lead and the pulse-generator encapsulation.

According to a further embodiment the intracorporeal ECG is measured between a ring electrode located outside the heart on one of the endocardial heart electrode leads and the pulse generator encapsulation.

According to a further embodiment multi-channel intracorporeal sensing is performed between a short non-endocardial electrode lead, one or more endocardial ring electrodes and the pulse generator encapsulation.

According to a further embodiment a back-up pulse is delivered to at least one of the ventricular electrodes if the intracorporeal ECG does not indicate an evoked R-wave.

According to a further embodiment the disclosed intracorporeal ECG analyzer is incorporated in an Implantable Cardioverter Defibrillator, ICD.

DESCRIPTION OF THE DRAWINGS

FIG. 1 schematically shows a known implanted biventricular pacemaker system.

FIG. 2 schematically shows an implanted biventricular pacemaker system with intracorporeal ECG monitoring through a short intracorporeal non-endocardial ECG monitoring electrode lead.

FIG. 3 schematically shows an implanted biventricular pacemaker system with intracorporeal ECG monitoring through an electrode dot located on the implanted pulse generator.

FIG. 4 schematically shows an implanted biventricular pacemaker system with intracorporeal ECG monitoring through ring electrodes placed on the endocardial heart electrode leads.

FIG. 8 shows a detailed block diagram of intracorporeal ECG analyzer.

DESCRIPTION OF THE PREFERRED EMBODIMENTS

Figure 5:
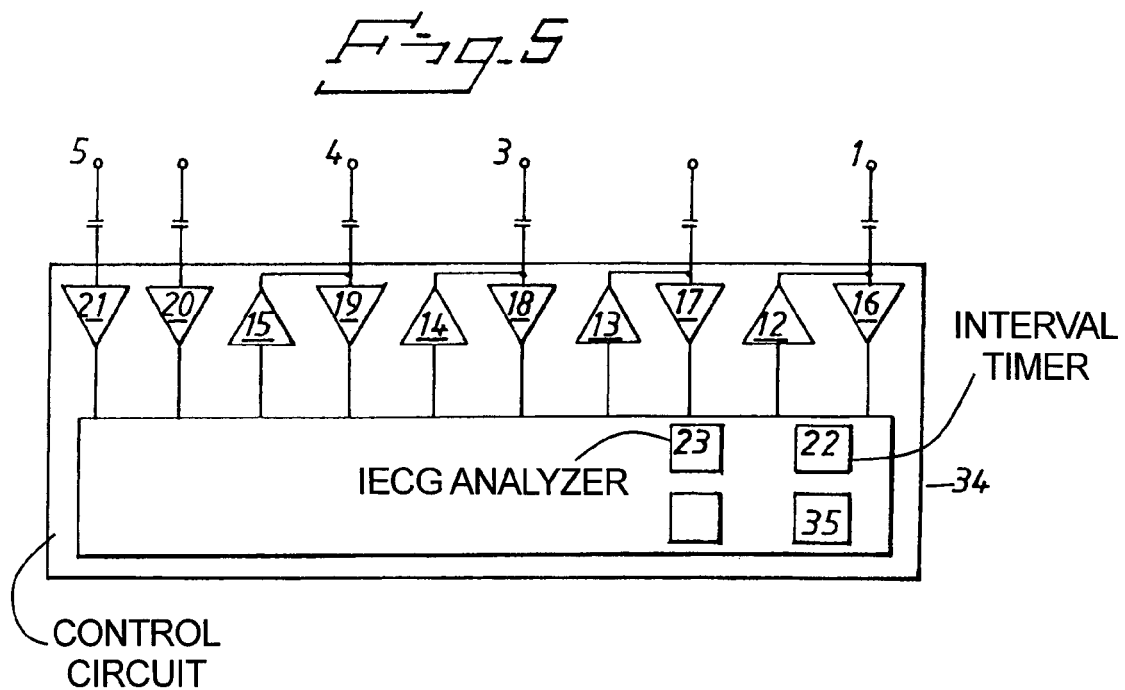
FIG. 5 is a schematic drawing of a control circuit in an implantable medical device according to the invention.

FIG. 1 shows a known biventricular pacemaker system as implanted. In this example an atrial heart electrode lead 1 is provided for atrial sensing/pacing by the implanted pulse generator 2. Further a left ventricular heart electrode lead 3 is provided for left ventricular sensing/pacing. The heart electrode lead 3 is implanted via the coronary sinus vein to a preferred position epicardially on the left ventricle. For right ventricular sensing/pacing a conventional right ventricular heart electrode lead 4 is provided. In some embodiments a fourth (not shown) left atrial heart electrode lead is provided for left atrial sensing/pacing.

FIG. 2 shows a biventricular pacemaker according to the invention as implanted. A short non-endocardial electrode lead 6 is provided for sensing an intracorporeal ECG from a position outside of the heart. In FIG. 2 it is assumed that the intracorporeal ECG is sensed between the pulse generator 5 encapsulation and the short non-endocardial electrode lead 6. There may be several short non-endocardial electrode leads to provide several different intracorporeal ECG sensing configurations. In the absence of intrinsic atrial event signals pacing pulses are delivered to the atrial heart electrode lead 1. Following an atrial sensed/paced event an AV interval is initiated. At the end of the AV interval pacing pulses are delivered to the right ventricular heart electrode lead 4 and to the left ventricular heart electrode lead 3. Following the delivery of the ventricular pacing pulses an evoked intracorporeal QRS is sensed via the short non-endocardial electrode lead 6 and the pulse generator 5 encapsulation. The implanted pulse generator 5 performs an analysis of the evoked intracorporeal QRS to determine if biventricular capture is present or if there is loss on one or both of the ventricular heart electrode leads (3,4). Criteria to determine capture or not may be evoked QRS duration or morphological criteria such as surface under the positive and negative deflection of the evoked QRS or the order in which negative and positive deflections occur or the duration of the most significant deflection in the evoked intracorporeal ECG signal. An intracorporeal ECG configuration similar to configuration V1 or CR1 in a surface ECG is an advantageous configuration even though any configuration can be used with appropriate adaptation of the analysis of the intracorporeal ECG signal. Surface ECG configuration CR1 is recorded from a measuring point located in the middle of the chest with the right arm as indifferent while V1 uses the same measuring point but the indifferent is from a point that is connected via three identical resistors connected to the left arm, right arm and the left leg. It is of course not possible to achieve exactly the same measurement configuration in an intracorporeal ECG as in a surface ECG. Generally an intracorporeal ECG configuration that provides a good visibility of the electrical activity of both ventricles is favorable. In V1 or CR1 the electrical activity of both ventricles are clearly visible and therefore a loss of capture in any of the left or right ventricles can easily be detected in V1 or CR1 by analyzing the evoked electrical activity from the pacing pulses.

FIG. 3 shows a biventricular pacemaker according to the invention. An intracorporeal ECG sensing electrode dot 7 is placed on the connector top of the pulse generator 8 and the intracorporeal ECG is sensed between the electrode dot 7 and the encapsulation of the pulse generator 8. This configuration will provide a relatively short distance of a few cm between the electrode dot 7 and the pulse generator encapsulation, which serves as the indifferent electrode. This will result in a lower signal amplitude but this can be compensated by a higher amplification of the picked up signal. In order to obtain several configurations of the intracorporeal ECG several electrode dots can be placed on the encapsulation and on the connector top of the pulse generator 8. Regarding the function of the pulse generator 8 the description for FIG. 2 is applicable also for FIG. 3.

FIG. 4 shows a biventricular pacemaker according to the invention. One or more of the endocardial heart electrode leads 1, 3, 4 is provided with ring electrodes such as 9, 10 to be placed outside the heart for sensing an intracorporeal ECG. A particularly advantageous method to connect the ring electrodes 9, 10 to the control unit of the pulse generator 11 may be to use a proposed electrode lead connector standard, IS-4, which may provide 4 individual contacts for each IS-4 connector. The intracorporeal surface ECG can be obtained between the pulse generator 11 encapsulation and any of the ring electrodes 9,10 or between the ring electrodes 9, 10. This will provide several configurations for intracorporeal ECG sensing.

FIG. 5 shows a block diagram of a control circuit 34 used in the pulse generator 2, 5, 8 and 11. The control circuit includes pacing pulse output circuits 12, 13, 14, 15 for delivering stimulation pulses to heart electrode leads 1, 3, 4. The control circuit 34 is adapted for a general pacing system configuration where right and left atria as well as right and left ventricles are paced and sensed. However in many cases the pacing system has one atrial heart electrode lead and two ventricular heart electrode leads. The control circuit 34 further has sense amplifiers and detectors 16, 17, 18, 19 for sensing atrial and ventricular activity respectively. Sense amplifiers 20 and 21 are used for sensing an intracorporeal ECG signal from locations outside of the heart. The control circuit 34 also includes an interval timer 22 that enables the delivery of stimulating pulses to the first ventricular electrode lead 3 and the second ventricular electrode lead 4 within the same heart cycle such that there is a time interval dT between the stimulating pulses. The time interval dT may be varied.

Furthermore the control circuit 34 in the present invention has an analyzer 23 for analyzing the intracorporeal ECG signal obtained via sense amplifiers 20 and 21. The analysis may include QRS duration, QRS morphology, duration of most significant deflection, or ST segment visibility. From the analysis it can be determined if there is capture on both ventricles via heart electrode leads 3 and 4 or if there is loss on one or both of the ventricles. If there is loss on both ventricles no intracorporeal evoked QRS will be present and a back-up pacing pulse to one or both ventricles will be emitted by pacing pulse output circuits 14, 15.

Figure 6:
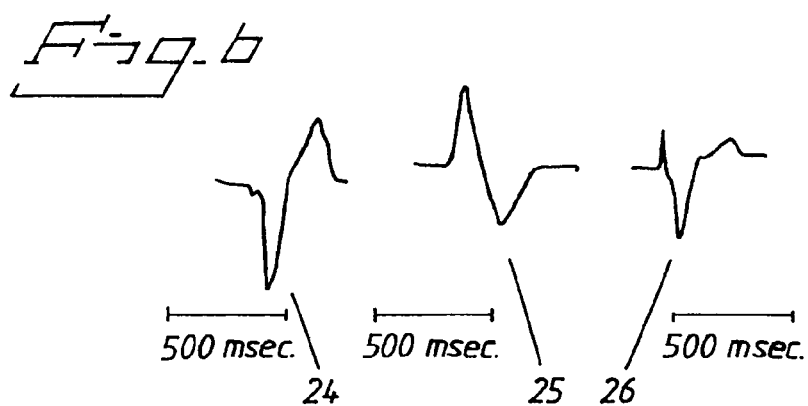
FIG. 6 shows examples of a typical surface ECGs for right ventricular pacing, left ventricular pacing and biventricular pacing, respectively.

FIG. 6 shows samples of surface ECG (V1) obtained during pacing. Complex 24 is obtained during right ventricular pacing (RV pacing), complex 25 is obtained during left ventricular pacing (LV pacing), while complex 26 is obtained during biventricular simultaneous right and left ventricular stimulation. As can be seen in surface ECG configuration V1 the order of deflections are opposite when comparing LV and RV pacing.

It is thus possible to determine if there is left ventricular loss of capture which will give an intracorporeal ECG similar to complex 24 in FIG. 6 that is obtained during right ventricular pacing. Similarly an intracorporeal ECG similar to complex 25 in FIG. 6 indicates right ventricular loss of capture. Biventricular capture yields a surface ECG similar to complex 26 in FIG. 6. As can be seen the QRS duration is significantly shorter compared to left or right ventricular pacing when biventricular capture is present. Further the order of deflections is reversed when comparing left and right capture. A morphology analysis of the intracorporeal ECG may be adapted to indicate loss of capture on any ventricular heart electrode lead and further determine if the loss was on the left or right ventricular heart electrode lead. Other ECG configurations can also be employed for analyzing evoked QRS characteristics that indicate capture of the right or left or both ventricles.

When biventricular pacing is applied the QRS is significantly shortened, the QRS has a unique morphology, and there is a visible S-T segment.

An intracorporeal ECG obtained from a location just under the skin is similar to a surface ECG obtained from a similar location on the surface of the skin. The surface ECG shows a greater variability due to polarization and contact problems with the ECG electrodes. This problem is not present with electrodes located under the skin for intracorporeal sensing of the ECG signal. Thus an intracorporeal ECG signal shows a better stability compared to a normal surface ECG signal. Some of the proposed intracorporeal ECG configurations use sensing electrode locations that are deeper into the body than subcutaneous which will cause some variation of the signal morphology of the intracorporeal ECG compared to a normal surface ECG. However it is always the distance and direction to the heart that determines the potential that an ECG sensing electrode will see regardless of whether it is located inside of the body or on the body surface. Once the intracorporeal sensing electrodes are placed the obtained signal morphology from the implanted intracorporeal electrodes may be analyzed to determine criteria to be used for determination of biventricular capture, left ventricular loss or right ventricular loss.

Figure 7:
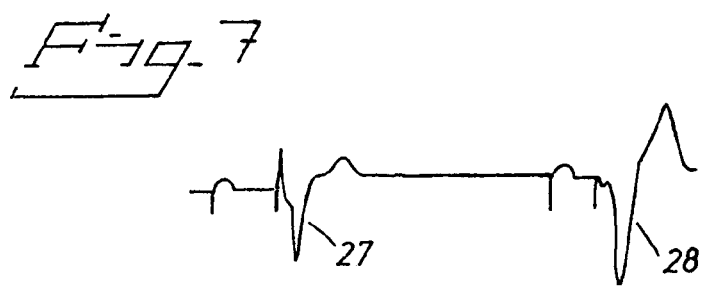
FIG. 7 shows an example of a typical ECG with right atrial stimulation and biventricular stimulation with one example of left ventricular loss.

FIG. 7 shows a schematic ECG indicating the function of a biventricular pacemaker utilizing the invention. In the first complex 27 an atrial stimulation pulse is indicated followed by biventricular stimulation pulses that are followed by the evoked QRS. The evoked QRS showed is obtained from surface ECG lead V1 but a similar signal can be obtained through electrode leads implanted under the skin at a location close to the corresponding surface ECG lead.

The evoked QRS is analyzed by the analyzer 23 in the control circuit. In complex 27 there is biventricular capture and no change of stimulation amplitude is required. In complex 28 the morphology indicates that there is a loss of capture on the left ventricular electrode lead since the complex morphology is similar that of right ventricular pacing. In the following cycle the pacemaker may just increase the output amplitude on the left ventricular output to accommodate for any threshold change. Another possibility is to execute a full threshold search procedure because of the changed threshold.

FIG. 8 shows a block diagram for the analyzer 23 for analyzing the intracorporeal ECG signal. The incoming intracorporeal ECG signal is A/D converted by A/D converter 36. Reference signals representing biventricular capture; right ventricular capture or left ventricular capture are stored in reference memory 37. The data stored in reference memory 37 may be obtained as an average of several heart complexes in order to improve noise suppression. The updating of the reference memory may either be manual under physician control or automatically controlled by the pulse generator itself. For each stimulated beat the evoked intracorporeal ECG signal is compared by comparison means 38 with a reference signal representing biventricular capture, right ventricular capture, left ventricular capture. The comparison means may for example calculate the sum of the squared difference between the reference and the actual signal for each sample of the signal. The reference signal that gives lowest squared sum is judged to be of the same type as the actual signal. After determination of in which heart chamber the loss has occurred the amplitude of the pacing pulses can be adjusted accordingly. This method is relatively computationally intensive and it may be feasible to use this method only at certain occasions. An alternative method may be to measure the QRS duration of the evoked intracorporeal ECG. A QRS duration measurement circuit 39 for this purpose may include, for example, a timer, which starts when the intracorporeal QRS deviates by a certain amount from the baseline and stops when the intracorporeal QRS has returned to a value close to the baseline. The interval recorded by such a timer comprised by QRS duration means will represent the duration of the intracorporeal QRS. A prolonged intracorporeal QRS duration indicates that biventricular capture is lost. In response to this observation the controller may initiate a morphology comparison in order to find out if there was loss on the right or left ventricle. Alternatively the pacing amplitudes to the right and left ventricles may be adjusted in an iterative search process until the duration of the evoked intracorporeal QRS has reached the normal duration. Another possibility would be to analyze the sequence of positive and negative peaks in the intracorporeal ECG to determine if biventricular, right ventricular or left ventricular capture is present. For this purpose a peak sequence detector 40 in the analyzer 23 records, for every stimulated beat, the sequence of positive and negative peaks in the intracorporeal QRS. The reference memory 37 contains the sequence of positive and negative peaks for biventricular and right and left ventricular capture. The reference memory 37 is updated to contain representative sequences in the same fashion as described above. A comparator 38, for each stimulated heart beat, determines if there was biventricular capture or if there was right or left ventricular capture. This determination will allow the control circuit 34 to change the stimulation amplitude on the right or left ventricular channel if necessary to maintain biventricular captures. Another possibility would be to analyze the sequence of positive and negative slopes in the intracorporeal QRS to determine if biventricular, right ventricular or left ventricular capture is present. A slope detector 41 in the analyzer 23 records, for every stimulated beat, the sequence of positive and negative slopes in the intracorporeal QRS. The reference memory contains the sequence of positive and negative slopes for biventricular and right and left capture. The reference memory 37 is updated to contain representative sequences is the same fashion as described above. The comparator 38, for each stimulated heart beat, determines if there was biventricular capture or if there was right or left ventricular capture. This determination will allow the controller 23 to change the stimulation amplitude on the right or left ventricular channel if necessary to maintain biventricular capture.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable biventricular cardiac stimulating device comprising:
   a housing adapted for implantation in a living subject;
   a pulse generating circuit contained in said housing for generating pacing pulses each having an energy content;
   a first electrode connected to said pulse generating circuit and adapted for positioning to interact with a first ventricle of the heart of the subject to deliver said pacing pulses thereto;
   a second electrode connected to said pulse-generating circuit adapted for positioning to interact with a second ventricle of the heart to deliver said pacing pulses thereto;
   a control circuit connected to said pulse generating circuit for controlling operation of said pulse generating circuit to control delivery of said pacing pulses to said first and second ventricles;
   a further electrode, remote from said housing, connected to said control circuit and adapted for positioning in the subject at a distance from the heart; and
   said control circuit sensing, via said further electrode, at least one intracorporeal ECG signal after delivery of pacing pulses to said first and second ventricles, respectively, and said control circuit analyzing at least one characteristic in said intracorporeal ECG signal to determine whether a loss of capture has occurred on either of said first and second electrodes.

2. An Implantable biventricular cardiac stimulating device as claimed in claim 1 wherein said control circuit analyzes said intracorporeal ECG signal to determine on which of said first and second electrodes said loss of capture has occurred.

3. An implantable biventricular cardiac stimulating device as claimed in claim 2 wherein, if said loss of capture has occurred, said control circuit adjusts the energy content of said pacing pubes to eliminate said loss of capture.

4. An implantable biventricular cardiac stimulating device as claimed in claim 1 wherein said control circuit analyzes a QRS duration in said intracorporeal ECG signal said characteristic.

5. An implantable biventricular cardiac stimulating device as claimed in claim 1 wherein said control circuit analyzes QRS morphology in said intracorporeal ECG signal as said characteristic.

6. An implantable biventricular cardiac stimulating device as claimed in aim 5 wherein said control circuit analyzes said QRS morphology by comparing the QRS morphology in the sensed intracorporeal ECG signal to stored data to identify said QRS morphology as indicating biventricular capture, right ventricular capture or left ventricular capture.

7. An implantable biventricular cardiac stimulating device as claimed in claim 1 wherein said control circuit analyzes a sequence of positive and negative peaks in said intracorporeal ECG as said characteristic.

8. An implantable biventricular cardiac stimulating device as claimed in claim 1 wherein said control circuit analyzes a sequence of positive and negative slopes in said intracorporeal ECG signal as said characteristic.

9. An implantable biventricular cardiac stimulating device as claimed in claim 1 wherein said control circuit analyzes said intracorporeal ECG signal for a presence or absence of a visible ST segment as said characteristic.

10. An implantable biventricular cardiac stimulating device as claimed in claim 1 wherein said control circuit employs said housing as an electrode, in combination with said further electrode, for sensing said intracorporeal ECG signal.

11. An implantable biventricular cardiac stimulating device as claimed in claim 1 wherein said further electrode comprises a short non-endocardial electrode lead.

12. An implantable biventricular cardiac stimulating device as claimed in claim 1 comprising at least one electrode dot disposed on said housing, and wherein said control circuit uses said at least one electrode dot, in combination with said further electrode, for sensing said intracorporeal ECG.

13. An implantable biventricular cardiac stimulating device as claimed in claim 1 wherein at least one of said first and second electrodes is a tip electrode of endocardial electrode lead, and wherein said further electrode comprises a ring electrode disposed on said endocardial lead and wherein said control circuit senses said intracorporeal ECG between said ring electrode and said tip electrode.

14. An implantable biventricular cardiac stimulating device as claimed in claim 1 wherein said control circuit operates said pulse generating circuit to deliver at least one back-up pulse to at least one of said first and second ventricles if said analysis of said intracorporeal ECG signal indicates a complete loss of capture.

* * * * *